(12) United States Patent
Neidle et al.

(10) Patent No.: US 11,560,380 B2
(45) Date of Patent: Jan. 24, 2023

(54) SUBSTITUTED NAPHTHALENE DIIMIDES AND THEIR USE

(71) Applicant: UCL Business Ltd, London (GB)

(72) Inventors: Stephen Neidle, London (GB); Richard Angell, London (GB); Sally Oxenford, London (GB)

(73) Assignee: UCL Business Ltd, London (GB)

( * ) Notice: Subject to any disclaimer, the term of this patent is extended or adjusted under 35 U.S.C. 154(b) by 0 days.

(21) Appl. No.: 17/611,890

(22) PCT Filed: May 15, 2020

(86) PCT No.: PCT/GB2020/051195
§ 371 (c)(1),
(2) Date: Nov. 16, 2021

(87) PCT Pub. No.: WO2020/229840
PCT Pub. Date: Nov. 19, 2020

(65) Prior Publication Data
US 2022/0220108 A1    Jul. 14, 2022

(30) Foreign Application Priority Data
May 16, 2019   (GB) ..................... 1906914

(51) Int. Cl.
*C07D 471/04* (2006.01)
*A61P 35/00* (2006.01)

(52) U.S. Cl.
CPC .......... *C07D 471/04* (2013.01); *A61P 35/00* (2018.01)

(58) Field of Classification Search
CPC ............................ C07D 471/04; A61K 35/00
USPC ..................................................... 514/232.5
See application file for complete search history.

(56) References Cited

U.S. PATENT DOCUMENTS

2014/0275065 A1   9/2014   Coate et al.

FOREIGN PATENT DOCUMENTS

| WO | 2009/068916 | 6/2009 |
| WO | 2017/103587 | 6/2017 |
| WO | WO 2017/103587 A1 | 6/2017 |

OTHER PUBLICATIONS

Gann et al., Journal of Materials Chemistry A: Materials for Energy and Sustainability (2017), 5(24), 12266-12277.*
Doria et al., "Hybrid ligand-alkylating agents targeting telomeric G-quadruplex structures", Organic & Biomolecular Chemistry, vol. 10, No. 14, Jan. 1, 2012, p. 2798.
Nadai et al., "Assessment of gene promoter G-quadruplex binding and modulation by a naphthalene diimide derivative in tumor cells", International Journal of Oncology, vol. 46, No. 1, Jan. 1, 2015, pp. 369-380.
Ohnmacht et al., "A G-quadruplex-binding compound showing anti-tumour activity in an in vivo model for pancreatic cancer", Scientific Reports, vol. 5, No. 1, Jun. 16, 2015.
Rigo, R. et al., "G-quadruplexes in human promoters: A challenge for therapeutic applications", Biochimica et Biophysica Acta, vol. 1861, pp. 1399-1413, (2017).
Bisht, S. et al., "Animal models for modeling pancreatic cancer and novel drug discovery", Expert Opinion on Drug Discovery, vol. 14, No. 2, pp. 127-142, (2019).
Ahmed, A.A. et al., "Asymmetrically substituted quadruplex-binding naphthalene diimide showing potent activity in pancreatic cancer models", ACS Medicinal Chemistry Letters, vol. 11, pp. 1634-1644, (2020).
Vo, T. et al., "Substituted naphthalenediimide compounds bind selectively to two human quadruplex structures with parallel topology", ACS Medicinal Chemistry Letters, vol. 11, 991-999, (2020).
Gkionis, K. et al., "Derivation of reliable geometries in QM calculations of DNA structures: Explicit solvent QM/MM and restrained implicit solvent QM optimizations of g-quadruplexes", Journal of Chemical Theory and Computation, vol. 12, pp. 2000-2016, (2016).

(Continued)

*Primary Examiner* — Niloofar Rahmani
(74) *Attorney, Agent, or Firm* — Evan Law Group LLC

(57) ABSTRACT

The present invention relates to naphthalene diimides, NDIs, and methods of synthesising them. The NDIs have DNA-quadruplex binding and stabilising activity, and potential in treatment of pancreatic, prostate, and other human cancers. The NDIs are a compound of Formula I.

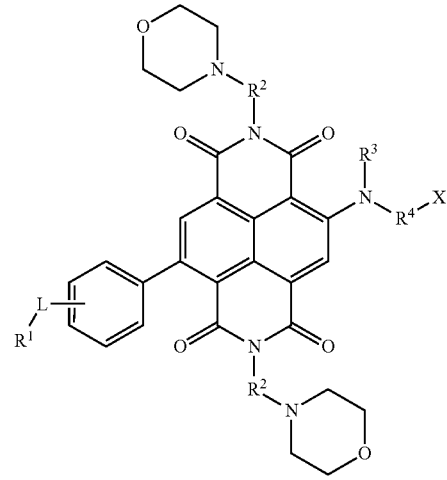

Formula I

18 Claims, 1 Drawing Sheet

(56) References Cited

OTHER PUBLICATIONS

Mitchell, T. et al., "Downregulation of androgen receptor transcription by promoter g-quadruplex stabilization as a potential alternative treatment for castrate-resistant prostate cancer", Biochemistry, vol. 52, pp. 1429-1436, (2013).

Gunaratnam, M. et al., "Targeting pancreatic cancer with a G-quadruplex ligand", Bioorganic & Medicinal Chemistry, vol. 19, pp. 7151-7157, (2011).

Gunaratnam, M. et al., "A naphthalene diimide G-quadruplex ligand inhibits cell growth and down-regulates BCL-2 expression in an imatinib-resistant gastrointestinal cancer cell line", Bioorganic & Medicinal Chemistry, vol. 26, pp. 2958-2964, (2018).

Hampel, S.M. et al., "Tetrasubstituted naphthalene diimide ligands with selectivity for telomeric G-quadruplexes and cancer cells", Bioorganic & Medicinal Chemistry Letters, vol. 20, pp. 6459-6463, (2010).

Doria, F. et al., "Hybrid ligand-alkylating agents targeting telomeric G-quadruplex structures", Organic & Biomolecular Chemistry, vol. 10, pp. 2798-2806, (2012).

Chaignon, F. et al., "Very large acceleration of the photoinduced electron transfer in a Ru(bpy)$_3$-naphthalene bisimide dyad bridged on the naphthyl core" Chemical Communications, pp. 64-66, (2007).

Asamitsu, S. et al., "Ligand design to acquire specificity to intended G-Quadruplex structures", Chemistry A European Journal, vol. 25, pp. 417-430, (2019).

Mendes, E. et al., "Combining 1,3-Ditriazolylbenzene and quinoline to discover a new G-quadruplex-interactive small molecule active against cancer stem-like cells", ChemMedChem, vol. 14, pp. 1325-1328, (2019).

Zyner, K.G. et al., "Genetic interactions of G-quadruplexes in humans", Elife, vol. 8, pp. 1-40, (2019).

Simone, R. et al., "G-quadruplex-binding small molecules ameliorate C9orf72 FTD/ALS pathology in vitro and in vivo", EMBO Molecular Medicine, vol. 10, No. 1, pp. 22-31, (2018).

Huppert, J.L. et al., "Prevalence of quadruplexes in the human genome", Nucleic Acids Research, vol. 33, No. 9, pp. 2908-2916, (2005).

Huppert, J.L. et al., "G-quadruplexes in promoters throughout the human genome", Nucleic Acids Research, vol. 35, No. 2, pp. 406-413, (2007).

Bugaut, A. et al., "5'UTR RNA G-quadruplexes: translation regulation and targeting", Nucleic Acids Research, vol. 40, No. 11, pp. 4727-4741, (2012).

Henderson, A. et al., "Detection of G-quadruplex DNA in mammalian cells", Nucleic Acids Research, vol. 42, No. 2, pp. 860-869, (2014).

Hopkins, Jr., H.P. et al., "Enthalpy and entropy changes for the intercalation of small molecules to DNA. I. substituted naphthalene monoimides and naphthalene diimides", Journal of Solution Chemistry, vol. 15, No. 7, pp. 563-579, (1986).

Nadai, M. et al., "Assessment of gene promoter G-quadruplex binding and modulation by a naphthalene diimide derivative in tumor cells", International Journal of Oncology, vol. 46, pp. 369-380, (2015).

Gunaratnam, M. et al., "Targeting human gastrointestinal stromal tumor cells with a quadruplex-binding small molecule", Journal of Medicinal Chemistry, vol. 52, No. 12, pp. 3774-3783, (2009).

Micco, M. et al., "Structure-based design and evaluation of naphthalene diimide G-quadruplex ligands as telomere targeting agents in pancreatic cancer cells", Journal of Medicinal Chemistry, vol. 56, pp. 2959-2974, (2013).

Neidle, S., "Quadruplex nucleic acids as novel therapeutic targets", Journal of Medicinal Chemistry, vol. 59, pp. 5987-6011, (2016).

Marchetti, C. et al., "Targeting multiple effector pathways in pancreatic ductal adenocarcinoma with a G-quadruplex-binding small molecule", Journal of Medicinal Chemistry, vol. 61, pp. 2500-2517, (2018).

Lim, K.W et al., "Coexistence of two distinct G-quadruplex conformations in the hTERT promoter", Journal of the American Chemical Society, vol. 132, p. 12331-12342, (2010).

Collie, G.W. et al., "Structural basis for telomeric G-quadruplex targeting by naphthalene diimide ligands", Journal of the American Chemical Society, vol. 134, pp. 2723-2731, (2012).

Javadinia, S.A. et al., "Therapeutic potential of targeting the Wnt/β-catenin pathway in the treatment of pancreatic cancer", Journal of Cellular Biochemistry, vol. 120, No. 5, pp. 6833-6840, (2019).

Thalacker, C. et al., "Synthesis and optical and redox properties of core-substituted naphthalene diimide dyes", The Journal of Organic Chemistry, vol. 71, pp. 8098-8105, (2006).

Lerner, L.K. et al., "Replication of G quadruplex DNA", Genes, vol. 10, No. 2, pp. 1-25, (2019).

Lu, X. et al., "Near-IR core-substituted naphthalenediimide fluorescent chemosensors for zinc ions: Ligand effects on PET and ICT channels", Chemistry—A European Journal, vol. 16, No. 28, pp. 8355-8364, (2010).

Pirota, V. et al., "Naphthalene diimides as multimodal G-quadruplex-selective ligands", Molecules, vol. 24, No. 3, pp. 1-26, (2019).

Todd, A.K. et al., "Highly prevalent putative quadruplex sequence motifs in human DNA", Nucleic Acids Research, vol. 33, No. 9, pp. 2901-2907, (2005).

Burge, S. et al., "Quadruplex DNA: sequence, topology and structure", Nucleic Acids Research, vol. 34, No. 19, pp. 5402-5415, (2006).

Balasubramanian, S. et al., "Targeting G-quadruplexes in gene promoters: a novel anticancer strategy?", Nature Reviews Drug Discovery, vol. 10, No. 4, pp. 261-275, (2011).

Bailey, P. et al., "Genomic analyses identify molecular subtypes of pancreatic cancer", Nature, vol. 531, pp. 47-52, (2016).

Biffi, G. et al., "Quantitative visualization of DNA G-quadruplex structures in human cells", Nature Chemistry, vol. 5, pp. 182-186, (2013).

Hansel-Hertsch, R. et al., "G-quadruplex structures mark human regulatory chromatin", Nature Genetics, vol. 48, No. 10, pp. 1267-1272, (2016).

Deer, E.L. et al., "Phenotype and genotype of pancreatic cancer cell lines", Pancreas, vol. 39, No. 4, pp. 425-435, (2010).

Decker, P. et al., "Inhibition of caspase-3-mediated poly(ADP-ribose) polymerase (PARP) apoptotic cleavage by human PARP autoantibodies and effect on cells undergoing apoptosis", The Journal of Biological Chemistry, vol. 275, No. 12, pp. 9043-9046, (2000).

Hingorani, S.R. et al., "Trp53$^{R172H}$ and Kras$^{G12D}$ cooperate to promote chromosomal instability and widely metastatic pancreatic ductal adenocarcinoma in mice", Cancer Cell, vol. 7, pp. 469-483, (2005).

Steele, C.W. et al., "CXCR2 inhibition profoundly suppresses metastases and augments immunotherapy in pancreatic ductal adenocarcinoma", Cancer Cell, vol. 29, pp. 832-845, (2016).

Raphael, B.J. et al., "Integrated genomic characterization of pancreatic ductal adenocarcinoma", Cancer Cell, vol. 32, pp. 185-203, (2017).

Taieb, J. et al., "First-line and second-line treatment of patients with metastatic pancreatic adenocarcinoma in routine clinical practice across Europe: a retrospective observational chart review study", ESMO Open, vol. 5, No. 1, pp. 1-8, (2020).

Song, J.H. et al., "Small-molecule-targeting hairpin loop of hTERT promoter G-quadruplex induces cancer cell death", Cell Chemical Biology, vol. 26, pp. 1110-1121, (2019).

Spiegel, J. et al., "The structure and function of DNA G-quadruplexes", Trends in Chemistry, vol. 2, No. 2, pp. 123-136, (2020).

Siddiqui-Jain, A. et al., "Direct evidence for a G-quadruplex in a promoter region and its targeting with a small molecule to repress c-MYC transcription", Proceeding of the National Academy of Science, vol. 99, No. 18, pp. 11593-11598, (2002).

Montoya, J.J. et al., "In vitro activity of a G-quadruplex-stabilizing small molecule that synergizes with navitoclax to induce cytotoxicity in acute myeloid leukemia cells", BMC Cancer, vol. 19, No. 1, pp. 1-11, (2019).

(56) References Cited

OTHER PUBLICATIONS

Van Wietmarschen, N. et al., "BLM helicase suppresses recombination at G-quadruplex motifs in transcribed genes", Nature Communications, vol. 9, No. 1, pp. 1-12, (2018).
Calabrese, D.R. et al., "Chemical and structural studies provide a mechanistic basis for recognition of the MYC G-quadruplex", Nature Communications, vol. 9, No. 1, pp. 1-15, (2018).
Wang, Y. et al., "G-quadruplex DNA drives genomic instability and represents a targetable molecular abnormality in ATRX-deficient malignant glioma", Nature Communications, vol. 10, No. 1, pp. 1-14, (2019).
Varshney, D. et al., "The regulation and functions of DNA and RNA G-quadruplexes", Molecular Cell Biology, vol. 21, No. 8, pp. 459-474, (2020).
Ohnmacht, S.A. et al., "A G-quadruplex-binding compound showing anti-tumor activity in an in vivo model for pancreatic cancer", Scientific Reports, vol. 5, No. 1, pp. 1-11, (2015).
Ahmed, A.A. et al., "A G-quadruplex-binding compound shows potent activity in human gemcitabine-resistant pancreatic cancer cells", Scientific Reports, vol. 10, No. 1, pp. 1-11, (2020).
Sissi, C. et al., "Tri-, tetra- and heptacyclic perylene analogues as new potential antineoplastic agents based on DNA telomerase inhibition", Bioorganic & Medicinal Chemistry, vol. 15, pp. 555-562, (2007).
Van Quaquebeke, E. et al., "2,2,2-trichloro-N-({2-[2-(dimethylamino)ethyl]-1,3-dioxo-2,3-dihydro-1H-benzo[de]isoquinolin-5-yl}carbamoyl)acetamide (UNBS3157), a novel nonhematotoxic naphthalimide derivative with potent antitumor activity", Journal of Medicinal Chemistry, vol. 50, No. 17, pp. 4122-4134, (2007).
International Search Report dated Jun. 7, 2020 for PCT application No. PCT/GB2020/051195.
Micco, M. et al., "Structure-guided optimization of tetra-substituted naphthalene diimide G-quadruplex compounds leads to enhanced potency in cancer cell lines", Poster Presented at the American Association for Cancer Research meeting, Chicago, Apr. 1, 2012.
Bondarenko, E.F. et al., "Studiesof naphthalene-1,4,5,8-tetracarboxylicacid derivatives. I. Naphthalene-1,4,5,8-tetracarboxylic acid bisimides", Zhurnal Organicheskoi Khimii, vol. 15, No. 12, pp. 2520-2525, (1979). Abstract only.
Brana, M.F. et al., "Naphthalimides as anti-cancer agents: Synthesis and biological activity", Current Medicinal Chemistry—Anti-Cancer Agents, vol. 1, No. 3, pp. 237-255, (2001).
"Benzo[lmn] [3, 8] phenanthroline-1, 3, 6, 8 (2H, 7H)-tetrone, 2, 7-bis (2-hydroxyethyl)-4, 9-bis [(2-hydroxyethyl)amino ]", Retrieved from Database Registry Chemical Abstract Service 2001; STN Database: Accession No. 321942-77-2.
Pub Chem Compound Summary, "CID 70680052", pp. 1-7, found at https://pubchem.ncbi.nlm.nih.gov/compound/70680052, (2022).
Pub Chem Compound Summary, "4,9-Bis{[3-(4-Methylpiperazin-1-Yl)propyl]amino}-2,7-Bis[3-(Morpholin-4-Yl)propyl]benzo[lmn][3.8]phenanthroline-1,3,6,8(2h,7h)-Tetrone", pp. 1-17, found at https://pubchem.ncbi.nlm.nih.gov/compound/135566608, (2022).

* cited by examiner

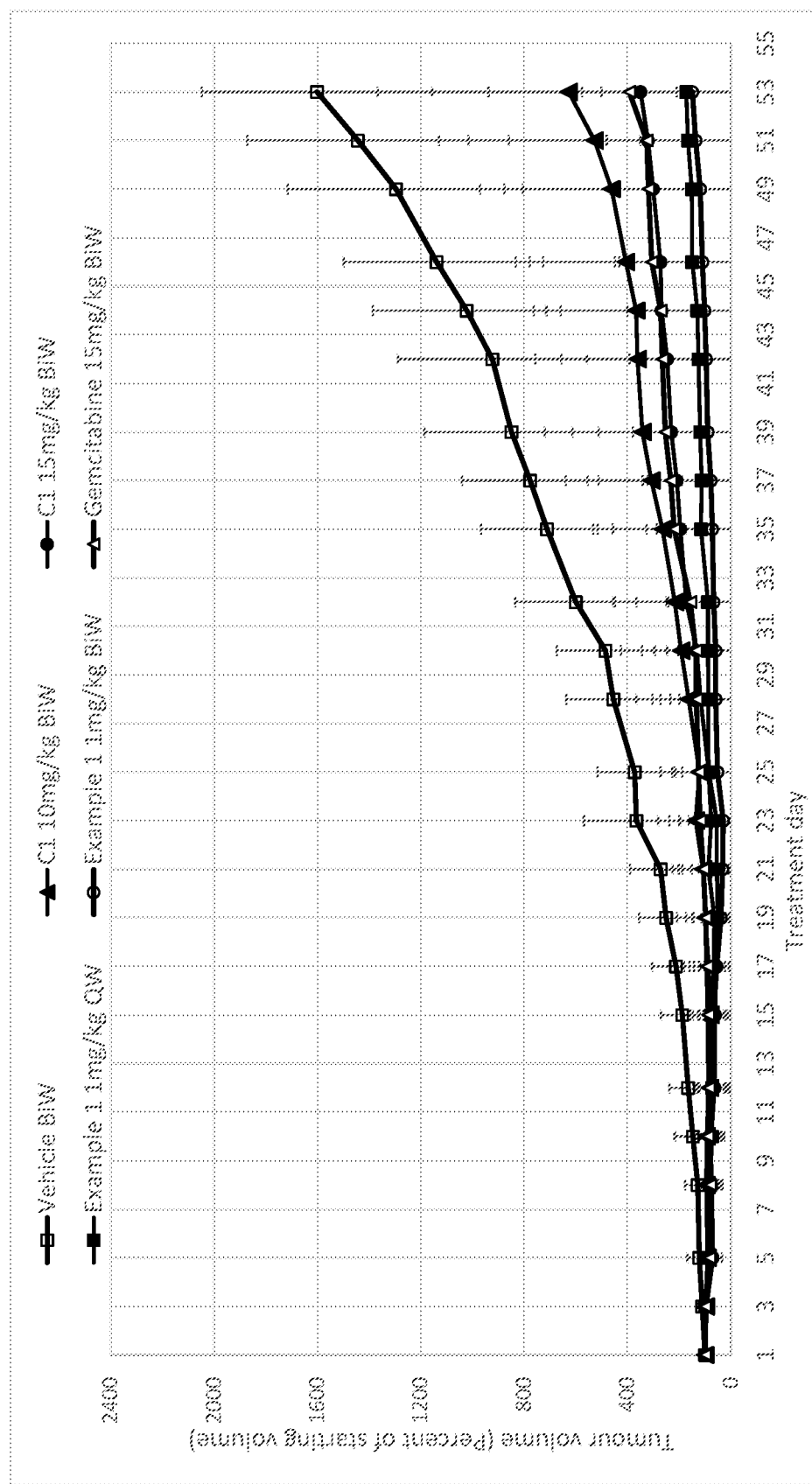

SUBSTITUTED NAPHTHALENE DIIMIDES AND THEIR USE

This application is the U.S. National Phase under 35 U.S.C. § 371 of International Application PCT/GB2020/051195, filed May 15, 2020, designating the U.S., and published as WO2020/229840, which claims priority to Great Britain Patent Application No. 1906914.5, filed May 16, 2019, the entire content of which is incorporated herein by reference.

FIELD OF THE INVENTION

The present invention relates to naphthalene diimides, NDIs, and methods of synthesising them. The NDIs have DNA-quadruplex binding and stabilising activity, and potential in treatment of pancreatic, prostate, and other human cancers.

BACKGROUND TO THE INVENTION

In WO2009/068916 we described tri- and tetra-substituted naphthalene diimides and processes for producing them. None of the exemplified products that were tri-substituted had different amino-functional ligands at equatorial and polar positions on the core ligand. The method said to be suited for producing tri-substituted compounds was based on the following schematic:

Schematic 1

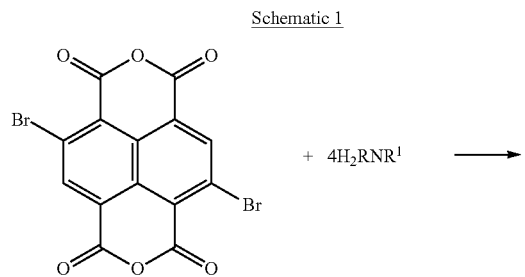

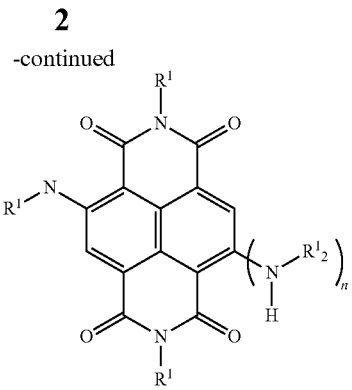

where $R^1$ is optionally substituted alkyl or aryl and n is 0 or 1. In practice a mixture of the tetra- (n=1) and tri-substituted (n=0) compounds was produced. All substituents, i.e. $R^1$ groups, are the same.

The specification describes methods for producing tetra-substituted compounds starting from the dichlorosubstituted analogue of the dibromo compound used above. The processes proceeded in one step, in which case the same $H_2NR^1$ reagent reacted at both anhydride groups and both —chlorine-substituted carbon to give 4 identical $R^1$ substituents on the product, or in two steps where in the first step a first reagent $H_2NR^2$ is reacted at both the anhydride groups and in a second step a second reagent $H_2NR^3$ is reacted at both chlorine-substituted carbon atoms. Compounds with basic substituents on the imide substituent and/or on the aromatic rings have strong DNA quadruplex binding properties.

In WO2017/103587 we described tri-substituted naphthalene diimides and processes for producing them. The method said to be suited for producing tri-substituted compounds was based on the following schematic:

Schematic 2

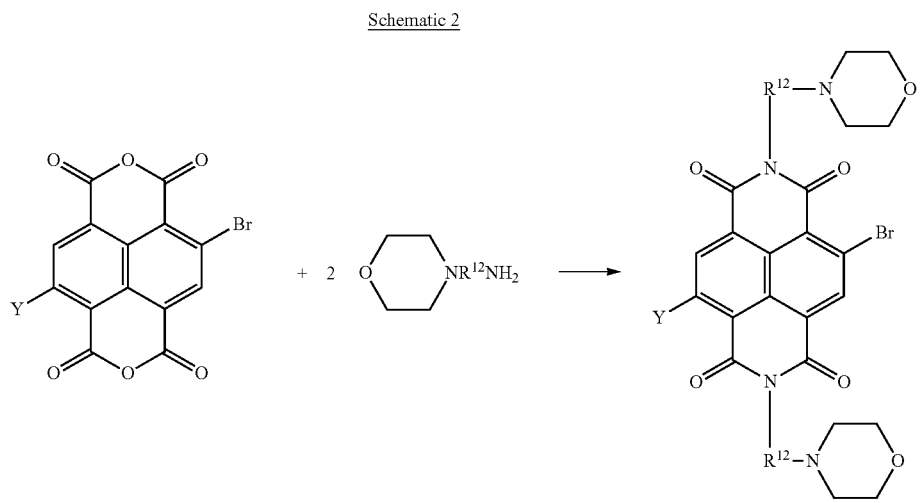

-continued

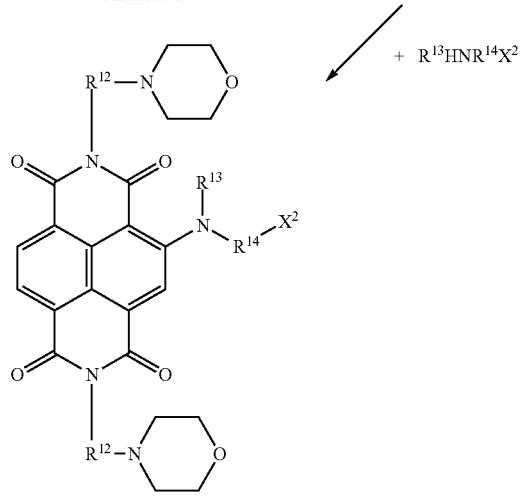

where Y is H or Br, the group $R^{12}$ are the same and are selected from the group consisting of straight and branched chain $C_{1-6}$ alkenediyl, $R^{13}$ is selected from the group consisting of H and $C_{1-6}$ alkyl, $R^{14}$ is selected from the group consisting of straight and branched chain $C_{1-6}$ alkanediyl and $C_{7-12}$ aralkanediyl, $X^2$ is selected from the group consisting of halo, $R^{11}$, $NR^{15}_2$, $CONR^{16}_2$, $COOR^{17}$, SH and $COR^{18}$, $R^{11}$ is selected from the group consisting of H, optionally substituted $C_{1-6}$ alkyl, optionally substituted $C_{5-7}$ cycloalkyl, $C_{5-7}$ heterocycloalkyl and aryl, each $R^{15}$ is selected from the group consisting of H, $C_{1-6}$ alkyl, aryl and $C_{7-12}$ aralkyl, N the groups $R^{15}$ together with the N-atom to which they are attached form a saturated heterocyclic ring of 5-7 atoms, each $R^{16}$ is selected from the group consisting of H and $C_{1-6}$ alkyl groups or the groups $R^{16}$ together with the N atom to which they are attached form a 5-7 membered heterocyclic ring, $R^{17}$ is selected from the group consisting of optionally substituted $C_{1-6}$ alkyl, $C_{7-12}$ aralkyl and aryl, $R^{18}$ is selected from the group consisting of optionally substituted $C_{1-6}$ alkyl, $C_{7-12}$ aralkyl and aryl, and whereby the Br atom or one of the or each Br atom is substituted by the nucleophilic amine nitrogen of the amine reagent to form the substituted NDI compound.

The tetra-substituted products, including products with groups $R^2$ different to groups $R^3$, have been tested in WO2009/068916, US2014-0275065A and in Hampel S. M. et al., Bioorg. Med. Chem. Lett. (2010) 20, 6459-6463, Micco. M., et al., J. Med. Chem. (2013) 56, 2959-2974, Collie, G. W., et al., J.A.C.S. (2012) 134, 2723-2731, Gunaratnam, M. et al., J. Med. Chem. (2009) 52, 3774-3783, Gunaratnam, M. et al., Bioorg. Med. Chem. (2011) 19, 7151-7157 and Mitchell, T. et al., Biochemistry (2013) 52, 1429-1436 for their binding properties to quadruplexes of telomeres and also those found in the promoter region of some genes. The data show the effective down-regulation of several proteins, the promoters of whose genes are targeted by the diimides, and hence result in growth inhibition of several cell-lines from a panel of cancer cell-lines. We have proposed in these publications to investigate further the impact of changing the nature of the substituent groups and the basicity of the tertiary amine groups in the cationic-substituents, on binding specificity and strength, and to investigate the potential of the compounds in cancer treatment, by testing models of cancers including pancreatic cancer.

In Scientific Reports (2015) 5:11385, Ohnmacht, S. A., et al., disclose the activity of 4,9-bis((3-(4-methylpiperazine-1-yl)-propyl)amino)-2,7-bis(3-morpholinopropyl)benzo[lmn][3,8]phenanthroline-1,3,6,8(2H,7H)-tetraone, also known as MM41, in vivo in a mouse model of human pancreatic cancer.

Nadai, M., et al., in Int. J. Oncol. (2015) 46, 369-380, disclose a tri-substituted naphthalene diimide compound, having 2-dimethylamino ethyl groups substituted at each imido nitrogen atom and having, as the third substituent a 2-(4-hydroxy-3-dimethyl amino methyl phenyl)ethyl amino group substituted at the 4-position on the NDI core. It has activity stabilising the telomeric G-quadruplex (GQ), causing telomere dysfunction and telomerase down regulation. Global gene expression on a panel of cell lines showed modulation of genes implicated in telomere function and mechanisms of cancer. However the authors conclude that direct evidence for the biological relevance of G-4s in the cell context is still lacking (Marchetti et al, J Med Chem, 2018, 61(6), pp. 2500-2517).

The synthesis of the tri-substituted compound reported by Nadai et al. is disclosed in Doria et al, Org Biomol. Chem, (2012) 10, 2798-2806.

SUMMARY OF THE INVENTION

It has surprisingly been found by the inventors that a particular group of side-chains on a tetra-substituted naphthalene diimide compound results in improved binding of the diimide compound to GQ resulting in improved anti-cancer activity.

Accordingly, in a first aspect of the invention there is provided a new compound of Formula I:

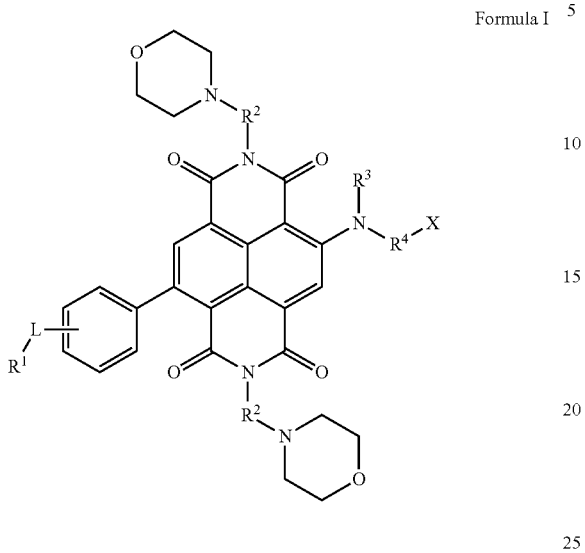

Formula I

L is in the meta or para position of the phenyl ring and is selected from the group consisting of $(CH_2)_{1-6}$ and $(CH_2)_{1-5}NH$;

$R^1$ is selected from the group consisting of optionally substituted $C_{5-7}$cycloalkyl, optionally substituted nitrogen-containing 5-7 membered heterocycloalkyl and $NR_9R_{10}$;

$R^2$ and $R^4$ are independently selected from the group consisting of straight and branched chain $C_{1-6}$-alkanediyl;

$R^3$, $R^9$ and $R^{10}$ are independently selected from the group consisting of H or $C_{1-6}$ alkyl;

X is selected from the group consisting of halo, $OR^5$, $NR^6_2$, $CONR^7_2$, $COOR^8$, H and $COR^8$;

$R^5$ is selected from the group consisting of H, $C_{1-6}$ alkyl, $C_{4-7}$ cycloalkyl, 4-7 membered heterocycloalkyl and aryl;

$R^6$ is selected from the group consisting of H, $C_{1-6}$ alkyl, aryl and, $C_{7-12}$-aralkyl, or the groups $R^6$ together with the N-atom to which they are attached form a N-containing, saturated 4-7 membered heterocyclic group; the groups $R^7$ are each selected from H and $C_{1-6}$ alkyl groups or the groups $R^7$ together with the N atom to which they are attached form a 4-7 membered heterocyclic group;

$R^8$ is selected from the group consisting of $C_{1-6}$ alkyl, $C_{7-12}$ aralkyl, and aryl; and salts, hydrates and solvates thereof.

The invention further provides the new compounds for use in a method of treatment of an animal to treat cancer or to inhibit the growth of a solid tumour, or to reduce the size of a solid tumour, for instance pancreatic and prostate tumours.

The invention also provides compositions containing the new compound and a diluent or carrier. The compositions are preferably pharmaceutical compositions and the carrier is then pharmaceutically acceptable.

In a second aspect of the invention there is provided a method for synthesising a substituted naphthalene diimide compound according to the first aspect of the invention, comprising the steps of:

i) reacting a compound of Formula IV in a nucleophilic substitution reaction with a compound of Formula V:

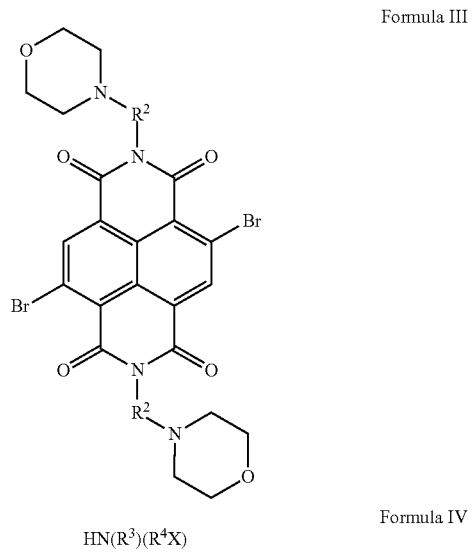

Formula III $HN(R^3)(R^4X)$

Formula IV wherein at least one Br in the compound of Formula III is substituted by the nucleophilic amine nitrogen in the compound of Formula IV;

ii) reacting a compound of Formula V, obtainable from the product resulting from the nucleophilic substitution reaction of Formula III and Formula IV, with a compound of Formula VI:

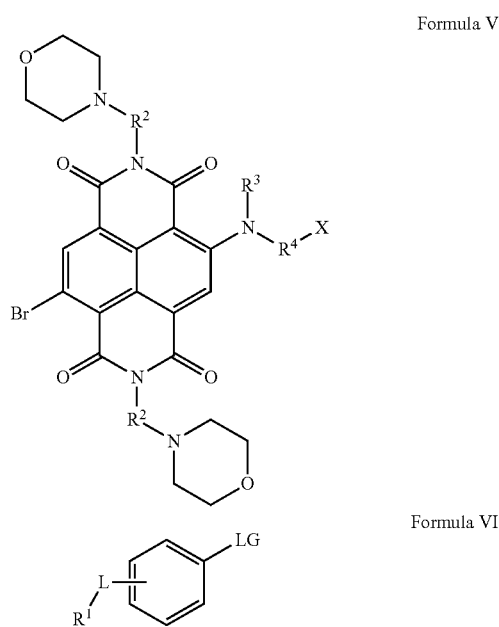

Formula V

Formula VI wherein an aryl-aryl bond is formed between the phenyl of Formula VI and the phenyl with the Br attached in the compound of Formula V, wherein the LG and Br are leaving groups, to make the compound of Formula I; and preferably iii) isolating the compound of Formula I from the product resulting from the reaction of Formula V and Formula VI;

wherein L, X and $R^1$ to $R^4$ are as defined for Formula I of the first aspect of the invention.

FIGURES

FIG. 1: Shows the tumour regression in a pancreatic cancer tumour in mice treated with a compound of the invention and comparative compounds.

DETAILED DESCRIPTION OF THE INVENTION

Definitions

As used herein, "alkyl", "cycloalkyl", "heterocycloalkyl", "heterocyclic", "aryl", and "aralkyl" groups may be monovalent or divalent unless otherwise specified.

As used herein, unless otherwise specified "aryl" means a monocyclic, bicyclic, or tricyclic monovalent or divalent (as appropriate) aromatic radical, such as phenyl, biphenyl, naphthyl, anthracenyl, which can be optionally substituted with up to three substituent.

As used herein, unless otherwise specified "optionally substituted" is with an of the substituents selected from the group of $C_1$-$C_6$ alkyl, hydroxy, $C_1$-$C_3$ hydroxyalkyl, $C_1$-$C_3$ alkoxy, $C_1$-$C_3$ haloalkoxy, amino, $C_1$-$C_3$ mono alkylamino, $C_1$-$C_3$ bis alkylamino, $C_1$-$C_3$ acylamino, $C_1$-$C_3$ aminoalkyl, mono ($C_1$-$C_3$ alkyl) amino $C_1$-$C_3$ alkyl, bis($C_1$-$C_3$ alkyl) amino $C_1$-$C_3$ alkyl, $C_1$-$C_3$-acylamino, $C_1$-$C_3$ alkyl sulfonylamino, halo, nitro, cyano, trifluoromethyl, carboxy, $C_1$-$C_3$ alkoxycarbonyl, aminocarbonyl, mono $C_1$-$C_3$ alkyl aminocarbonyl, bis $C_1$-$C_3$ alkyl aminocarbonyl, —$SO_3H$, $C_1$-$C_3$ alkylsulfonyl, aminosulfonyl, mono $C_1$-$C_3$ alkyl aminosulfonyl and bis $C_1$-$C_3$-alkyl aminosulfonyl.

As used herein, unless otherwise specified "heterocycloalkyl" and "heterocyclic" groups are carbocyclic radicals containing up to 4 heteroatoms selected from oxygen, nitrogen and sulfur. They may be bicyclic or monocyclic. They are preferably saturated. If the heterocycle is a divalent linker, the heterocycle may be attached to neighbouring groups through a carbon atom, or through one of the heteroatoms, e.g. a N. Examples of heterocycles are pyrrolidine, piperazine, and morpholine.

Preferred Groups of the Invention

In the first aspect of the invention, L is preferably $(CH_2)_{1-6}$, preferably $(CH_2)_{1-4}$, more preferably $(CH_2)_{1-3}$, yet more preferably $(CH_2)_{1-2}$, even more preferably $(CH_2)$. Preferably L is in the para position of the phenyl. When $R^1$ is the optionally substituted nitrogen-containing 5-7 membered heterocycloalkyl or the $NR_9R_{10}$, it is preferable that $R^1$ is joined to L via the nitrogen atom of $R^1$.

It is envisaged that L or $R^1$ comprises a basic nitrogen atom. As such, $R^1$ may be any group that comprises a basic nitrogen atom. $R^1$ is preferably a nitrogen-containing 5-7 membered heterocycloalkyl, preferably a nitrogen-containing 5-6 membered heterocycloalkyl, more preferably a nitrogen-containing 5 membered heterocycloalkyl. Preferably the nitrogen of the nitrogen-containing 5-7 membered heterocycloalkyl is the only heteroatom in the heterocycloalkyl. In another aspect, the nitrogen-containing 5-7 membered heterocycloalkyl comprises a second heteroatom, such as an oxygen atom.

Suitably the nitrogen-containing 5-7 membered heterocycloalkyl is selected from the group consisting of pyrrolidinyl, imidazolidinyl, pyrazolidinyl, piperidinyl, piperazinyl, morpholinyl, azepanyl, diazepanyl, preferably pyrrolidinyl. Suitably L is $(CH_2)$ and $R^1$ is pyrrolidinyl.

Suitably $R^1$ is $NR_9R_{10}$. $R^9$ and $R^{10}$ are independently selected from the group consisting of H or $C_{1-6}$ alkyl, preferably $C_{1-6}$ alkyl, more preferably $C_{2-4}$ alkyl, even more preferably $C_{2-3}$ alkyl. Suitably the $NR_9R_{10}$ is diethylamino, dipropylamino or ethylpropylamino.

In another embodiment, L comprises the basic nitrogen atom. Suitably L is $(CH_2)_{1-5}NH$, preferably $(CH_2)_{1-3}NH$, more preferably $(CH_2)_{1-2}NH$, even more preferably $(CH_2)NH$ and $R^1$ is a $C_{5-7}$cycloalkyl, preferably a $C_5$cycloalkyl. Preferably L is in the para position of the phenyl.

Both $R^2$ groups in Formula I are the same as one another. $R^2$ is preferably straight chain $C_{2-4}$-alkanediyl, most preferably straight chain $C_3$-alkanediyl. $R^4$ may or may not be the same as $R^2$, and is preferably straight or branched chain $C_{2-4}$-alkanediyl, most preferably $C_2$-alkanediyl.

X preferably comprises an amine group, i.e. X is preferably $NR^6_2$ or $CONR^7_2$, further preferably $NR^6_2$. The groups $R^6$ and $R^7$ together with the N-atom to which they are attached preferably form a N-containing, saturated 4-7 membered heterocyclic group, further preferably a N-containing, saturated 5 membered heterocyclic group. Of such compounds, those where the two groups $R^6$ are linked to form a heterocycle are preferred as they seem to have useful cytotoxic activity in cancer cell line tests. X is most preferably a saturated pyrrolidinyl group.

Preferably, Formula I has the following structure of Formula II:

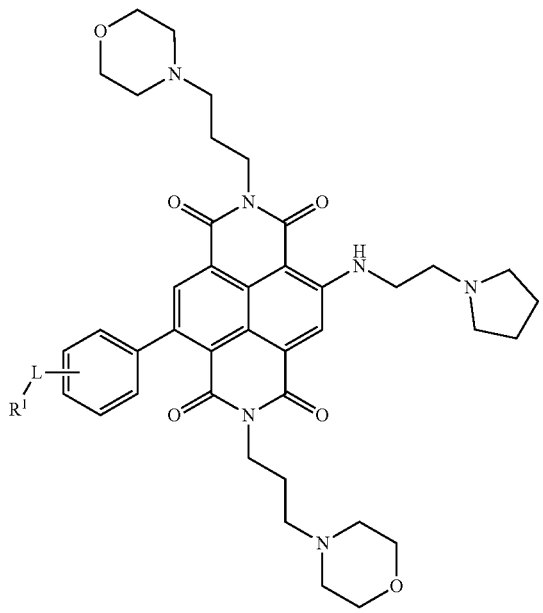

Formula II wherein L and $R^1$ are as defined for Formula I, with any of the preferred groups as outlined above.

Suitably the compound is selected from the group consisting of: 2,7-bis(3-morpholinopropyl)-4-((2-(pyrrolidin-1-yl)ethyl)amino)-9-(4-(pyrrolidin-1-ylmethyl)phenyl)benzo[lmn][3,8]phenanthroline-1,3,6,8(2H,7H)-tetraone; 4-(4-(morpholinomethyl)phenyl)-2,7-bis(3-morpholinopropyl)-9-((2-(pyrrolidin-1-yl)ethyl)amino)benzo[lmn][3,8]phenanthroline-1,3,6,8(2H,7H)-tetraone; 2,7-bis(3-morpholinopropyl)-4-((2-(pyrrolidin-1-yl)ethyl)amino)-9-(3-(pyrrolidin-1-ylmethyl)phenyl)benzo[lmn][3,8]phenanthroline-1,3,6,8(2H,7H)-tetraone; 2,7-bis(3- morpholinopropyl)-4-(4-(piperidin-1-ylmethyl)phenyl)-9-((2-(pyrrolidin-1-yl)ethyl)amino)benzo[lmn][3,8]phenanthroline-1,3,6,8(2H,7H)-tetraone; 4-(4-((diethylamino)methyl)phenyl)-2,7-bis(3-morpholinopropyl)-9-((2-(pyrrolidin-1-yl)ethyl)amino)benzo[lmn][3,8]phenanthroline-1,3,6,8(2H,7H)-tetraone; 4-(4-((cyclopentylamino)methyl)phenyl)-2,7-bis(3-morpholinopropyl)-9-((2-(pyrrolidin-1-yl)ethyl)amino)benzo[lmn][3,8]phenanthroline-1,3,6,8(2H,7H)-tetraone; 4-(4-(azepan-1-ylmethyl)phenyl)-2,7-bis(3-morpholinopropyl)-9-((2-(pyrrolidin-1-yl)ethyl)amino)benzo[lmn][3,8]phenanthroline-1,3,6,8(2H,7H)-tetraone; 4-bromo-2,7-bis(3-morpholinopropyl)-9-((2-(pyrrolidin-1-yl)ethyl)amino)benzo[lmn][3,8]phenanthroline-1,3,6,8(2H,7H)-tetraone; and salts, hydrates and solvates thereof.

In the second aspect of the invention, L, X and $R^1$ to $R^4$ for Formula IV to Formula VIII are preferably as defined as the preferred features above for L, X and $R^1$ to $R^4$ of Formula I of the first aspect of the invention.

The method of the invention comprises a first step of reacting a brominated naphthalene diimide of Formula III with an amine reagent of Formula IV in an aromatic nucleophilic substitution reaction whereby the bromine atom is replaced by an amino group $N(R^3)(R^4X)$. The starting diimide is a dibromo compound, and the aromatic nucleophilic substitution reaction may result in both bromine atoms being replaced by an amine group or just one of them (i.e. a compound of Formula V), although it is preferred that just one of the bromines is replaced, and there must be at least one compound of Formula V produced. It is preferable to separate a mixture of both the singly and doubly substituted naphthalene diimide, for example by using column chromatography.

In a second step, the compound of Formula V produced in the first step is reacted with a reagent of Formula VI in a substitution reaction whereby the bromine atom is replaced by the phenyl in Formula VI via the carbon atom that the LG (leaving group) is attached to initially. In one aspect the LG may be a boronic acid group, however, the skilled person will appreciate there are multiple ways to undergo the substitution reaction and form the aryl-aryl bond between Formulas V and VI. As a result, at least one compound of Formula I is produced.

Preferably, in another step, the compound of Formula I is isolated by using column chromatography.

Preferably, the specific form of column chromatography used is selected from gel and flash column chromatography.

The compounds of the present invention may be provided in the form of pharmaceutically acceptable compositions. The compounds of the present invention, especially when presented in the form of acid addition salts, for instance where some or all of the basic amine groups are converted to salt form, are water soluble and have approximately neutral pH. As such these salts are suitable for administration in the form of aqueous solution, which would be appropriate for intravenous administration. The pharmaceutical aqueous solutions preferably comprise 1 to 500 mg/I, of the compound.

The compounds of the present invention may be provided in a form suitable to be made up into pharmaceutical compositions, for instance, in dried, rehydratable form, for instance with carrier or diluent. Such dried forms may be produced by crystallisation and/or evaporation. Alternatively, the compounds may be presented as concentrates, for instance in water or an organic, pharmaceutically acceptable, solvent for dilution before administration.

As used herein, a pharmaceutically acceptable salt is a salt with a pharmaceutically acceptable acid or base. Pharmaceutically acceptable acids include both inorganic acids such as hydrochloric, sulphuric, phosphoric, diphosphoric, hydrobromic or nitric acid and organic acids such as citric, fumaric, maleic, malic, ascorbic, succinic, tartaric, benzoic, acetic, methanesulfonic, ethanesulfonic, salicylic, stearic, benzenesulfonic or p-toluenesulfonic acid. Pharmaceutically acceptable bases include alkali metal (e.g. sodium or potassium) and alkali earth metal (e.g. calcium or magnesium) hydroxides and organic bases such as alkyl amines, aryl amines or heterocyclic amines.

For the avoidance of doubt, the present invention also embraces prodrugs which react in vivo to give a compound of the present invention.

Combinations according to the present invention may also be used in conjunction with other agents to inhibit undesirable and uncontrolled cell proliferation, for example antibodies. The compound may be conjugated to the antibody or administered as two separate components.

The compounds of the invention and compositions comprising them may be administered by any route. In one embodiment, a pharmaceutical composition comprising a compound of the invention may be formulated in a format suitable for oral, rectal, parenteral, intranasal or transdermal administration or administration by inhalation or by suppository. Typical routes of administration are parenteral, intranasal or transdermal administration or administration by inhalation. For chemotherapy of tumours, the compositions are most conveniently administered intravenously.

When used as treatment for existing tumours, the compounds of the present invention may be administered using regimens developed for chemotherapeutic agents.

The compounds of the invention and compositions have utility in treating subjects who have cancer. One particular class of cancers are known as solid tumours, in which a solid mass of cancerous material can be identified. Another class comprises haematological cancers, known as cancers that affect the blood system.

Specific types of cancers that can be treated using the compounds and compositions of the present invention include, but are not limited to prostate, pancreatic, small cell lung or gastro-intestinal. In a preferred embodiment, the cancer is prostate or pancreatic.

The compounds of the invention and compositions are useful in treatment to inhibit the growth of a solid tumour, or to reduce the size of a solid tumour, for example wherein the tumour is a pancreatic or prostate tumour.

The subject to be treated is suitably an animal, preferably a human.

As such, there is provided a method of treatment comprising administering to a subject a compound or pharmaceutical composition of the invention to treat cancer, particularly those already described above.

There is also provided a use of a compound or pharmaceutical composition of the invention in the manufacture of a medicament for the treatment of cancer, particularly those already described above.

The invention is further illustrated in the accompanying examples.

EXAMPLES

A series of tetrasubstituted naphthalene diimides have been synthesised and evaluated as G-quadruplex ligands, and as potential anti-cancer agents.

Chemistry

All chemicals, reagents, and solvents were purchased from commercial sources and used as received unless otherwise stated. Solvents were commercial HPLC grade unless dry solvent is specified, in which case the Aldrich 'Sure Seal' dry solvents were used. Column chromatography was performed on pre-packed silica (230-400 mesh, 40-63 μm) cartridges using the eluent indicated.

$^1$H NMR Spectra were acquired on a Bruker Avance III spectrometer at 400 MHz using residual undeuterated solvent as reference.

Analytical LCMS was carried out using either acidic or basic methods as follows:

Acidic, HPLC: Waters X-Select CSH C18, 2.5 μm, 4.6×30 mm column eluting with a gradient of 0.1% Formic acid in MeCN in 0.1% Formic acid in water. The gradient from 5-95% 0.1% Formic acid in MeCN occurs between 0.00-3.00 minutes at 2.5 ml/min with a flush from 3.01-3.5 minutes at 4.5 ml/min. A column re-equilibration to 5% MeCN is from 3.60-4.00 minutes at 2.5 ml/min. UV spectra of the eluted peaks were measured using an Agilent 1260 Infinity or Agilent 1200 VWD at 254 nm. Mass spectra were measured using an Agilent 6120 or Agilent 1956 MSD running with positive/negative switching or an Agilent 6100 MSD running in either positive or negative mode.

Basic, HPLC: Waters X-Select BEH C18, 2.5 μm, 4.6×30 mm column eluting with a gradient of MeCN in aqueous 10 mM ammonium bicarbonate. The gradient from 5-95% MeCN occurs between 0.00-3.00 minutes at 2.5 ml/min with a flush from 3.01-3.5 minutes at 4.5 ml/min. A column re-equilibration to 5% MeCN is from 3.60-4.00 minutes at 2.5 ml/min. UV spectra of the eluted peaks were measured using an Agilent 1260 Infinity or Agilent 1200 VWD at 254 nm. Mass spectra were measured using an Agilent 6120 or Agilent 1956 MSD running with positive/negative switching or an Agilent 6100 MSD running in either positive or negative mode.

Alternatively analytical UPLC/MS was carried out using either acidic or basic methods as follows:

Acidic, UPLC: Waters Acquity CSH C18, 1.7 μm, 2.1×30 mm column eluting with a gradient of 0.1% Formic acid in MeCN in 0.1% Formic acid in water. The gradient is structured with a starting point of 5% MeCN held from 0.0-0.11 minutes. The gradient from 5-95% occurs between 0.11-2.15 minutes with a flush from 2.15-2.56 minutes. A column re-equilibration to 5% MeCN is from 2.56-2.83 minutes. UV spectra of the eluted peaks were measured using an Acquity PDA and mass spectra were recorded using an Acquity QDa detector with ESI pos/neg switching.

Basic UPLC: Waters Acquity BEH C18, 1.7 μm, 2.1×30 mm column eluting with a gradient of MeCN in aqueous 10 mM Ammonium Bicarbonate. The gradient is structured with a starting point of 5% MeCN held from 0.0-0.11 minutes. The gradient from 5-95% occurs between 0.11-2.15 minutes with a flush from 2.15-2.56 minutes. A column re-equilibration to 5% MeCN is from 2.56-2.83 minutes. UV spectra of the eluted peaks were measured using an Acquity PDA and mass spectra were recorded using an Acquity QDa detector with ESI pos/neg switching.

Preparative HPLC was carried out using a Waters Xselect CSH C18, 5 μm, 19×50 mm column using either a gradient of either 0.1% Formic Acid in MeCN in 0.1% aqueous Formic Acid or a gradient of MeCN in aqueous 10 mM Ammonium Bicarbonate; or a Waters Xbridge BEH C18, 5 μm, 19×50 mm column using a gradient MeCN in aqueous 10 mM Ammonium Bicarbonate. Fractions were collected following detection by UV at a single wavelength measured by a variable wavelength detector on a Gilson 215 preparative HPLC or Varian PrepStar preparative HPLC; by mass and UV at a single wavelength measured by a ZQ single quadrupole mass spectrometer, with positive and negative ion electrospray, and a dual wavelength detector on a Waters FractionLynx LCMS.

Example 1: 2,7-bis(3-morpholinopropyl)-4-((2-(pyrrolidin-1-yl)ethyl)amino)-9-(4-(pyrrolidin-1-ylmethyl)phenyl)benzo[lmn][3,8]phenanthroline-1,3,6,8 (2H,7H)-tetraone

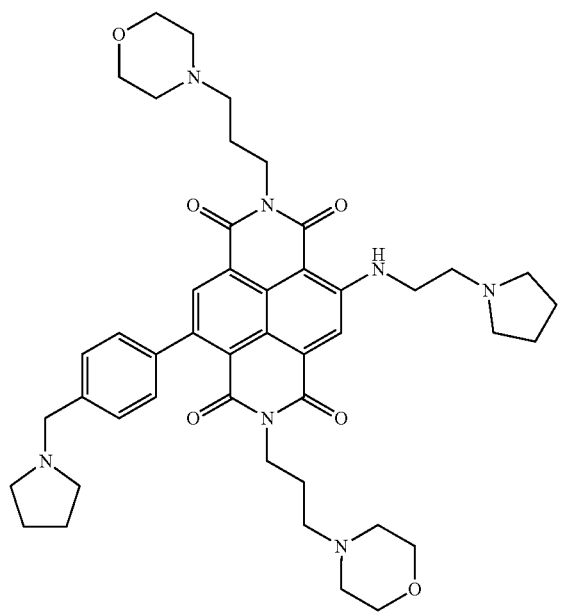 [SMILES: O=C1c2cc(-c3ccc(CN4CCCC4)cc3)c3c4c(cc(NCCN5CCCC5)c(c24)C(=O)N1CCCN1CCOCC1)C(=O)N(CCCN1CCOCC1)C3=O]

4-bromo-2,7-bis(3-morpholinopropyl)-9-((2-(pyrrolidin-1-yl)ethyl)amino)benzo[lmn][3,8]phenanthroline-1,3,6,8 (2H,7H)-tetraone (100 mg, 0.141 mmol), (3,5-dimethoxyphenyl)boronic acid (77 mg, 0.422 mmol) or 1-(4-(4,4,5,5-tetramethyl-1,3,2-dioxaborolan-2-yl)benzyl)pyrrolidine (121 mg, 0.422 mmol) and Pd(Ph3P)4 (8.12 mg, 7.03 μmol) were dissolved in THF/2M K$_2$CO$_3$ (3:1, 2 mL) and degassed, backfilling with nitrogen three times. The mixture was heated (70° C. block temperature) with stirring for 3 h. The reaction was cooled, diluted with DCM (15 mL), washed with water (15 mL), passed through a hydrophobic frit and concentrated in vacuo. The crude product was purified by preparative HPLC, Basic, 20-50 MeCN in Water to afford the title compound (7.1 mg, 8.34 μmol, 6% yield) as a dark red solid. 1H NMR (400 MHz, Chloroform-d) δ 10.24 (t, J=5.3 Hz, 1H), 8.48 (s, 1H), 8.32 (s, 1H), 7.52 (d, J=7.9 Hz, 2H), 7.38-7.29 (m, 2H), 4.34-4.25 (m, 2H), 4.21-4.07 (m, 2H), 3.87 (s, 2H), 3.75 (q, J=6.2 Hz, 2H), 3.62 (dt, J=16.8, 4.7 Hz, 8H), 2.95 (t, J=6.5 Hz, 2H), 2.78 (s, 4H), 2.71-2.64 (m, 4H), 2.53 (t, J=7.0 Hz, 2H), 2.50-2.35 (m, 10H), 2.02-1.78 (m, 12H). 1H NMR in CDCl$_3$ 1863-70-prep2 was consistent with product structure at 93% purity. LCMS, Basic, 1863-70B-prep, m/z 792.4 [M+H]$_+$ at 4 min, 96% purity @ 254 nm. Contains 4% CMO3 by LC @ 254 nm.

Example 2: 4-(4-(morpholinomethyl)phenyl)-2,7-bis(3-morpholinopropyl)-9-((2-(pyrrolidin-1-yl)ethyl)amino)benzo[lmn][3,8]phenanthroline-1,3,6,8(2H,7H)-tetraone

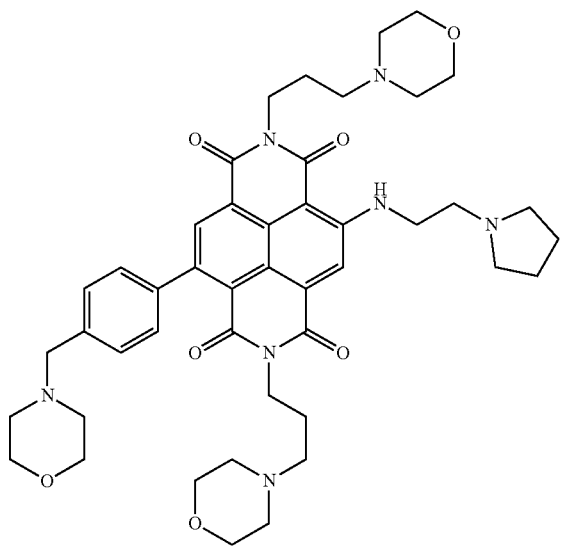 [SMILES: O=C1c2cc(-c3ccc(CN4CCOCC4)cc3)c3c4c(cc(NCCN5CCCC5)c(c24)C(=O)N1CCCN1CCOCC1)C(=O)N(CCCN1CCOCC1)C3=O]

A stirred mixture of 4-bromo-2,7-bis(3-morpholinopropyl)-9-((2-(pyrrolidin-1-yl)ethyl)amino)benzo[lmn][3,8]phenanthroline-1,3,6,8(2H,7H)-tetraone (202 mg, 0.284 mmol) and (4-(morpholinomethyl)phenyl)boronic acid (188 mg, 0.852 mmol) in dioxane (4 mL) was treated with potassium carbonate (568 µL of a 2 M aq solution, 1.135 mmol) and de-gassed. S-Phos Pd G3 (6.64 mg, 8.52 µmol) was added and the mixture again de-gassed then the whole heated to 80° C. (block temp, pre-heated). After 18 hr, the mixture was allowed to cool then diluted with water (10 mL) and sat aq NaHCO$_3$ (10 mL) and extracted with DCM (2×20 mL). The combined organics were dried over Na$_2$SO$_4$ and evaporated. Column chromatography (12 g Buchi FlashPure, pre-adsorbed, 10-70% [9:1 (1:1 THF:DCM): 7 M NH$_3$ in MeCOH] in (1:1 THF:DCM)) gave two cuts of moderately pure product. The centre of the product band was evaporated and taken up in MeCN (2 mL). After ~48 hr, this was filtered and the solid discarded. Meanwhile, material from the edge of the product band was evaporated and re-slurried from iso-hexanes. This material was combined with the MeCN liquors from the above batch and the resultant purified by column chromatography (12 g RediSep Gold, 30-70% (9:1 DCM: 0.7 M NH$_3$ in MeCOH) in DCM, loading in DCM). The central cut of this band was evaporated to afford the product as a bright red glassy solid (50 mg, 22%).

LCMS: Found m/z 808.3 (C$_{45}$H$_{58}$N$_7$O$_7$ (MH$^+$) requires 808.4) @ 6.68 min. $^1$H NMR (500 MHz, Chloroform-d) δ 10.24 (t, J=5.3 Hz, 1H), 8.50 (s, 1H), 8.33 (s, 1H), 7.45 (d, J=8.0 Hz, 2H), 7.32 (d, J=8.0 Hz, 2H), 4.30 (t, J=7.4 Hz, 2H), 4.15 (t, J=7.4 Hz, 2H), 3.83-3.71 (m, 6H), 3.65-3.59 (m, 10H), 2.95 (t, J=6.4 Hz, 2H), 2.70-2.67 (m, 4H), 2.58-2.50 (m, 6H), 2.47-2.40 (m, 10H), 1.96 (app p, J=7.1 Hz, 2H), 1.90-1.84 (m, 6H).

Example 3: 2,7-bis(3-morpholinopropyl)-4-((2-(pyrrolidin-1-yl)ethyl)amino)-9-(3-(pyrrolidin-1-ylmethyl)phenyl)benzo[lmn][3,8]phenanthroline-1,3,6,8(2H,7H)-tetraone

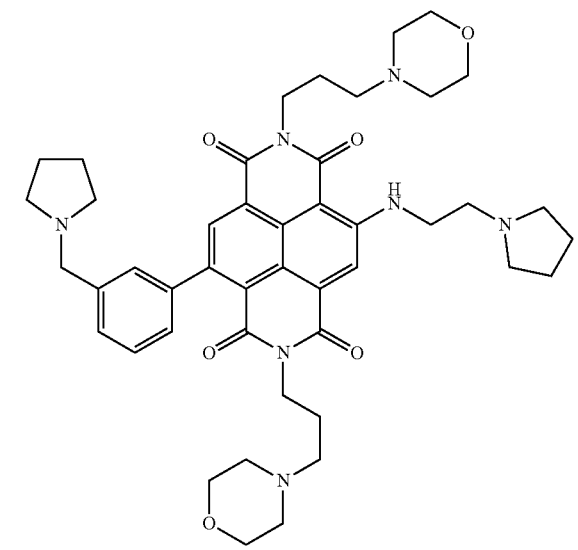 [SMILES: O=C1c2cc(-c3cccc(CN4CCCC4)c3)c3c4c(cc(NCCN5CCCC5)c(c24)C(=O)N1CCCN1CCOCC1)C(=O)N(CCCN1CCOCC1)C3=O]

A stirred mixture of 4-bromo-2,7-bis(3-morpholinopropyl)-9-((2-(pyrrolidin-1-yl)ethyl)amino)benzo[lmn][3,8]phenanthroline-1,3,6,8(2H,7H)-tetraone (149 mg, 0.209 mmol) and 1-(3-(4,4,5,5-tetramethyl-1,3,2-dioxaborolan-2-yl)benzyl)pyrrolidine (180 mg, 0.628 mmol) in dioxane (4 mL) was treated with potassium carbonate (419 µL of a 2 M aq solution, 0.837 mmol) and de-gassed. S-Phos Pd G3 (4.90 mg, 6.28 µmol) was charged, the mixture again de-gassed and the whole heated to 80° C. After 16 hr, the mixture was allowed to cool then diluted with water (10 mL) and sat aq NaHCO$_3$ (10 mL) and extracted with DCM (2×20 mL). The combined organics were dried over Na$_2$SO$_4$ and evaporated. Column chromatography (12 g RediSep Gold, 30-60% (9:1 DCM: 0.7 M NH$_3$ in MeCOH) in DCM, loading in DCM) gave product in moderate purity. The residue was purified by reverse phase column chromatography (12 g Reveleris C-18, 75-100% (70 mM NH$_3$ in MeCOH) in water), loading in DMSO) to afford product in better but still unsatisfactory purity. The residue was re-purified by reverse phase column chromatography (12 g Reveleris C-18, 75-100% (70 mM NH$_3$ in MeCOH) in water, loading in DMSO) to afford the product as a bright red glassy solid (16 mg, 10%).

LCMS: Found m/z 792.4: (C$_{45}$H$_{58}$N$_7$O$_8$ (MH$^+$) requires 792.4) @ 6.42 min. $^1$H NMR (500 MHz, Methylene Chloride-d$_2$) δ 10.26 (t, J=5.5 Hz, 1H), 8.47 (s, 1H), 8.35 (s, 1H), 7.47-7.37 (m, 2H), 7.35 (br s, 1H), 7.26 (dt, J=7.2, 1.7 Hz, 1H), 4.30 (t, J=7.4, 2H), 4.13 (t, J=7.4 Hz, 2H), 3.82-3.65 (m, 4H), 3.52-3.58 (m, 8H), 2.95 (t, J=6.2 Hz, 2H), 2.69-2.66 (m, 4H), 2.61-2.30 (m, 16H), 1.93 (p, J=6.9 Hz, 2H), 1.89-1.75 (m, 10H).

Example 4: 2,7-bis(3-morpholinopropyl)-4-(4-(piperidin-1-ylmethyl)phenyl)-9-((2-(pyrrolidin-1-yl)ethyl)amino)benzo[lmn][3,8]phenanthroline-1,3,6,8(2H,7H)-tetraone

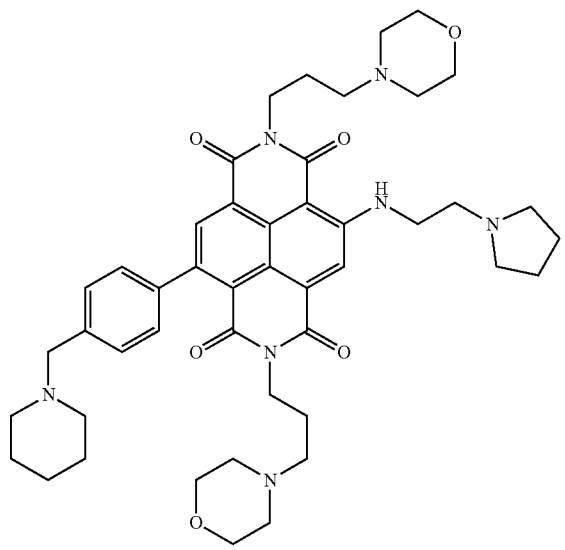 [SMILES: O=C1c2cc(-c3ccc(CN4CCCCC4)cc3)c3c4c(cc(NCCN5CCCC5)c(c24)C(=O)N1CCCN1CCOCC1)C(=O)N(CCCN1CCOCC1)C3=O]

A stirred mixture of 4-bromo-2,7-bis(3-morpholinopropyl)-9-((2-(pyrrolidin-1-yl)ethyl)amino)benzo[lmn][3,8]phenanthroline-1,3,6,8(2H,7H)-tetraone (155 mg, 0.218 mmol) and 1-(4-(4,4,5,5-tetramethyl-1,3,2-dioxaborolan-2-yl)benzyl)piperidine (197 mg, 0.653 mmol) in dioxane (4 mL) was treated with potassium carbonate (436 µL of a 2 M aq solution, 0.871 mmol) and de-gassed. S-Phos Pd G3 (5.10 mg, 6.53 µmol) was charged, the mixture again de-gassed and the whole heated to 80° C. After 16 hr, the mixture was allowed to cool then diluted with water (10 mL) and sat aq NaHCO₃ (10 mL) and extracted with DCM (2×20 mL). The combined organics were dried over Na₂SO₄ and evaporated. Column chromatography (12 g RediSep Gold, 30-60% (9:1 DCM: 0.7 M NH₃ in MeCOH) in DCM, loading in DCM) gave product in moderate purity. The residue was purified by reverse phase column chromatography (12 g Reveleris C-18, 75-100% (70 mM NH₃ in MeCOH) in water, loading in DMSO) to afford the product as a bright red glassy solid (61 mg, 35%).

LCMS: Found m/z 806.3: ($C_{46}H_{60}N_7O_6$ (MH⁺) requires 805.5) @ 7.38 min. ¹H NMR (500 MHz, Methylene Chloride-d₂) δ 10.25 (t, J=5.1 Hz, 1H), 8.47 (s, 1H), 8.34 (s, 1H), 7.43 (d, J=8.1 Hz, 2H), 7.33 (d, J=8.1 Hz, 2H), 4.29 (t, J=7.4 Hz, 2H), 4.14 (t, J=7.3 Hz, 2H), 3.75 (q, J=5.9 Hz, 2H), 3.64-3.50 (m, 10H), 2.95 (t, J=6.2 Hz, 2H), 2.69-2.66 (m, 4H), 2.56-2.29 (m, 16H), 1.93 (p, J=7.0 Hz, 2H), 1.89-1.82 (m, 6H), 1.68-1.62 (m, 4H), 1.53-1.49 (m, 2H).

Example 5: 4-(4-((diethylamino)methyl)phenyl)-2,7-bis(3-morpholinopropyl)-9-((2-(pyrrolidin-1-yl)ethyl)amino)benzo[lmn][3,8]phenanthroline-1,3,6,8(2H,7H)-tetraone

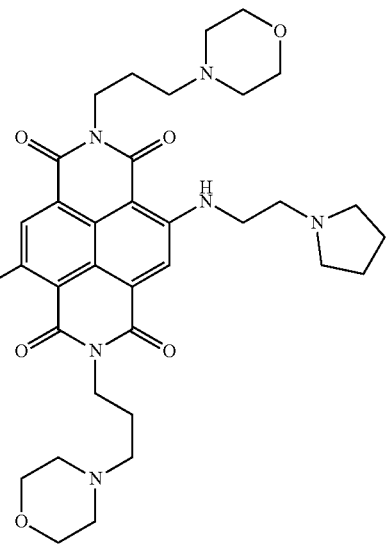

A stirred mixture of 4-bromo-2,7-bis(3-morpholinopropyl)-9-((2-(pyrrolidin-1-yl)ethyl)amino)benzo[lmn][3,8]phenanthroline-1,3,6,8(2H,7H)-tetraone (155 mg, 0.218 mmol) and N-ethyl-N-(4-(4,4,5,5-tetramethyl-1,3,2-dioxaborolan-2-yl)benzyl)ethanamine (189 mg, 0.653 mmol) in dioxane (4 mL) was treated with potassium carbonate (436 µL of a 2 M aq solution, 0.871 mmol) and de-gassed. S-Phos Pd G3 (5.10 mg, 6.53 µmol) was charged, the mixture again de-gassed and the whole heated to 80° C. After 16 hr, the mixture was allowed to cool then diluted with water (10 mL) and sat aq NaHCO₃ (10 mL) and extracted with DCM (2×20 mL). The combined organics were dried over Na₂SO₄ and evaporated. Column chromatography (12 g BuchiFlashPure, 30-60% (9:1 DCM: 1.4 M NH₃ in MeCOH) in DCM, loading in DCM) gave product in moderate purity. The residue was purified by reverse phase column chromatography (12 g Reveleris C-18, 75-100% (70 mM NH₃ in MeCOH) in water, loading in DMSO) to afford the product as a bright red glassy solid (81 mg, 47%).

LCMS: Found m/z 794.2: ($C_{45}H_{60}N_7O_6$ (MH⁺) requires 794.5) @ 6.93 min. ¹H NMR (500 MHz, Methylene Chloride-d₂) b 10.24 (t, J=5.2 Hz, 1H), 8.46 (s, 1H), 8.32 (s, 1H), 7.46 (d, J=8.0 Hz, 2H), 7.33 (d, J=8.0 Hz, 2H), 4.28 (t, J=7.4 Hz, 2H), 4.13 (t, J=7.4 Hz, 2H), 3.79-3.71 (m, 2H), 3.69 (s, 2H), 3.58-3.53 (m, 8H), 2.94 (t, J=6.2 Hz, 2H), 2.69-2.66 (m, 4H), 2.61 (q, J=7.1 Hz, 4H), 2.50 (t, J=6.8 Hz, 2H), 2.47-2.30 (m, 10H), 1.93 (p, J=6.9 Hz, 2H), 1.88-1.82 (m, 6H), 1.12 (t, J=7.1 Hz, 6H).

Example 6: 4-(4-((cyclopentylamino)methyl)phenyl)-2,7-bis(3-morpholinopropyl)-9-((2-(pyrrolidin-1-yl)ethyl)amino)benzo[lmn][3,8]phenanthroline-1,3,6,8(2H,7H)-tetraone

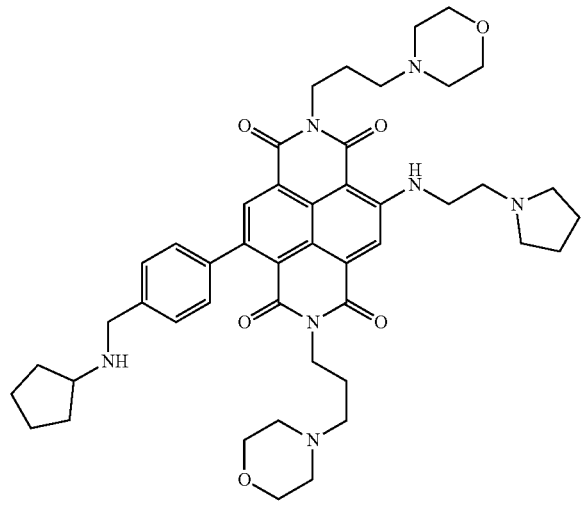 [SMILES: O=C1c2cc(-c3ccc(CNC4CCCC4)cc3)c3c4c(cc(NCCN5CCCC5)c(c24)C(=O)N1CCCN1CCOCC1)C(=O)N(CCCN1CCOCC1)C3=O]

Example 7: 4-(4-(azepan-1-ylmethyl)phenyl)-2,7-bis(3-morpholinopropyl)-9-((2-(pyrrolidin-1-yl)ethyl)amino)benzo[lmn][3,8]phenanthroline-1,3,6,8(2H,7H)-tetraone

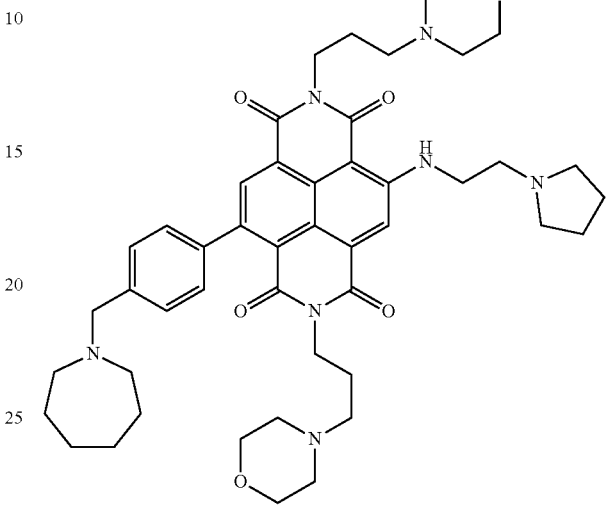

A stirred mixture of 4-bromo-2,7-bis(3-morpholinopropyl)-9-((2-(pyrrolidin-1-yl)ethyl)amino)benzo[lmn][3,8]phenanthroline-1,3,6,8(2H,7H)-tetraone (153 mg, 0.215 mmol) and N-(4-(4,4,5,5-tetramethyl-1,3,2-dioxaborolan-2-yl)benzyl)cyclopentanamine (194 mg, 0.645 mmol) in dioxane (4 mL) was treated with potassium carbonate (430 µL of a 2 M aq solution, 0.860 mmol) and de-gassed. S-Phos Pd G3 (5.03 mg, 6.45 µmol) was charged, the mixture again de-gassed and the whole heated to 80° C. After 16 hr, the mixture was allowed to cool then diluted with water (10 mL) and sat aq NaHCO$_3$ (10 mL) and extracted with DCM (2×20 mL). The combined organics were dried over Na$_2$SO$_4$ and evaporated. Column chromatography (12 g BuchiFlashPure, 30-60% (9:1 DCM: 1.4 M NH$_3$ in MeCOH) in DCM, loading in DCM) gave product in moderate purity. The residue was purified by reverse phase column chromatography (12 g Reveleris C-18, 75-100% (70 mM NH$_3$ in MeCOH) in water, loading in DMSO) to afford the product as a bright red glassy solid (29 mg, 17%).

LCMS: Found m/z 806.4: (C$_{46}$H$_{60}$N$_7$O$_6$ (MH$^+$) requires 805.5) @ 6.57 min. $^1$H NMR (500 MHz, Methylene Chloride-d$_2$) δ 10.25 (t, J=5.1 Hz, 1H), 8.46 (s, 1H), 8.34 (s, 1H), 7.45 (d, J=7.9 Hz, 2H), 7.33 (d, J=7.9 Hz, 2H), 4.29 (t, J=7.3 Hz, 2H), 4.13 (t, J=7.4, Hz, 2H), 3.88 (s, 2H), 3.75 (q, J=5.9 Hz, 2H), 3.58-3.53 (m, 8H), 3.23 (p, J=6.4 Hz, 1H), 2.95 (t, J=6.2 Hz, 2H), 2.69-2.66 (m, 4H), 2.50 (t, J=6.8 Hz, 2H), 2.47-2.30 (m, 10H), 1.96-1.89 (m, 4H), 1.88-1.80 (m, 6H), 1.79-1.72 (m, 2H), 1.65-1.58 (m, 2H), 1.51-1.42 (m, 2H), CH$_2$NHCH not observed.

A stirred mixture of 4-bromo-2,7-bis(3-morpholinopropyl)-9-((2-(pyrrolidin-1-yl)ethyl)amino)benzo[lmn][3,8]phenanthroline-1,3,6,8(2H,7H)-tetraone (223 mg, 0.313 mmol) and 1-(4-(4,4,5,5-tetramethyl-1,3,2-dioxaborolan-2-yl)benzyl)azepane (296 mg, 0.940 mmol) in dioxane (4 mL) was treated with potassium carbonate (627 µL of a 2 M aq solution, 1.253 mmol) and de-gassed. S-Phos Pd G3 (7.33 mg, 9.40 µmol) was charged, the mixture again de-gassed and the whole heated to 80° C. After 16 hr, the mixture was allowed to cool then diluted with water (10 mL) and sat aq NaHCO$_3$ (10 mL) and extracted with DCM (2×20 mL). The combined organics were dried over Na$_2$SO$_4$ and evaporated. Column chromatography (12 g Buchi FlashPure, 30-60% (9:1 DCM:1.4 M NH$_3$ in MeCOH) in DCM, loading in DCM) gave product in moderate purity. The residue was purified by reverse phase column chromatography (12 g Reveleris C-18, 75-100% (70 mM NH$_3$ in MeCOH) in water, loading in DMSO) to afford the product as a bright red glassy solid (130 mg, 51%).

LCMS: Found m/z 820.3: (C$_{47}$H$_{62}$N$_7$O$_6$ (MH$^+$) requires 820.5) @ 7.69 min. $^1$H NMR (500 MHz, Methylene Chloride-d$_2$) b 10.25 (t, J=5.1 Hz, 1H), 8.47 (s, 1H), 8.34 (s, 1H), 7.47 (d, J=7.8 Hz, 2H), 7.33 (d, J=7.8 Hz, 2H), 4.29 (t, J=7.4 Hz, 2H), 4.14 (t, J=7.3 Hz, 2H), 3.82-3.70 (m, 4H), 3.57-3.53 (m, 8H), 2.95 (t, J=6.2 Hz, 2H), 2.78-2.61 (m, 8H), 2.50 (t, J=6.8 Hz, 2H), 2.47-2.30 (m, 10H), 1.93 (p, J=7.0 Hz, 2H), 1.88-1.82 (m, 6H), 1.73-1.68 (m, 8H).

Example 8: 4-bromo-2,7-bis(3-morpholinopropyl)-9-((2-(pyrrolidin-1-yl)ethyl)amino)benzo[lmn][3,8]phenanthroline-1,3,6,8(2H,7H)-tetraone

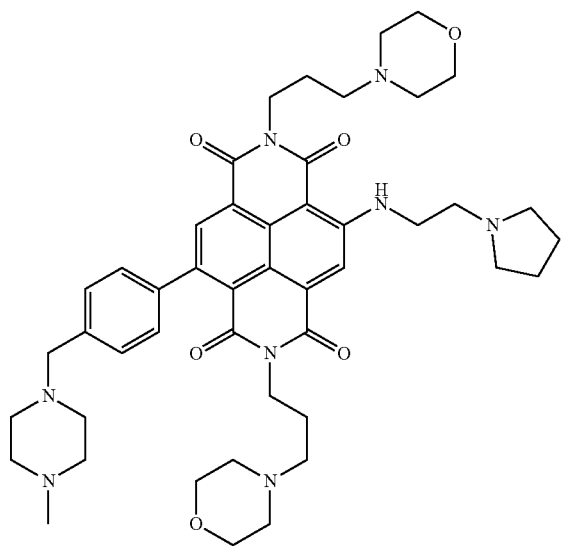

A stirred mixture of 4-bromo-2,7-bis(3-morpholinopropyl)-9-((2-(pyrrolidin-1-yl)ethyl)amino)benzo[lmn][3,8]phenanthroline-1,3,6,8(2H,7H)-tetraone (213 mg, 0.299 mmol) and 1-methyl-4-(4-(4,4,5,5-tetramethyl-1,3,2-dioxaborolan-2-yl)benzyl)piperazine (284 mg, 0.898 mmol) in dioxane (4 mL) was treated with potassium carbonate (599 μL of a 2 M aq solution, 1.197 mmol) and de-gassed. S-Phos Pd G3 (7.01 mg, 8.98 μmol) was charged, the mixture again de-gassed and the whole heated to 80° C. After 16 hr, the mixture was allowed to cool then diluted with water (10 mL) and sat aq $NaHCO_3$ (10 mL) and extracted with DCM (2×20 mL). The combined organics were dried over $Na_2SO_4$ and evaporated. Column chromatography (12 g BuchiFlashPure, 30-60% (9:1 DCM:3.5 M $NH_3$ in MeCOH) in DCM, loading in DCM) gave product in moderate purity. The residue was purified by reverse phase column chromatography (12 g Reveleris C-18, 75-100% (70 mM $NH_3$ in MeCOH) in water, loading in DMSO) to afford the product as a bright red glassy solid (111 mg, 45%).

LCMS: Found m/z 821.2: ($C_{46}H_{61}N_8O_6$ ($MH^+$) requires 821.5) @ 6.06 min. $^1$H NMR (500 MHz, Methylene Chloride-$d_2$) b 10.25 (t, J=5.1 Hz, 1H), 8.46 (s, 1H), 8.34 (s, 1H), 7.43 (d, J=8.1 Hz, 2H), 7.33 (d, J=8.1 Hz, 2H), 4.29 (t, J=7.4 Hz, 2H), 4.13 (t, J=7.3 Hz, 2H), 3.75 (q, J=5.9 Hz, 2H), 3.62 (s, 2H), 3.57-3.53 (m, 8H), 2.95 (t, J=6.2 Hz, 2H), 2.77-2.20 (m, 27H), 1.94 (q, J=7.1 Hz, 2H), 1.89-1.80 (m, 6H).

Biophysical and Cell Biology Data
Cell Proliferation Assay

The CellTiter 96® AQueous One Solution Cell Proliferation Assay (Invitrogen) is a colorimetric method for determining the number of viable cells in proliferation or cytotoxicity assays. The CellTiter 96® AQueous One Solution Reagent contains a novel tetrazolium compound [3-(4,5-dimethylthiazol-2-yl)-5-(3-carboxymethoxyphenyl)-2-(4-sulfophenyl)-2H-tetrazolium, inner salt; MTS] and an electron coupling reagent (phenazine ethosulfate; PES). PES has enhanced chemical stability, which allows it to be combined with MTS to form a stable solution. The MTS tetrazolium compound (Owen's reagent) is bioreduced by cells into a colored formazan product that is soluble in tissue culture medium. Assays are performed by adding a small amount of the CellTiter 96@ AQueous One Solution Reagent directly to culture wells, incubating for 1-4 hours and then recording the absorbance at 490 nm with a 96-well plate reader. The quantity of formazan product as measured by absorbance at 490 nm is directly proportional to the number of living cells in culture. The kit was used as per the manufacturers' instructions. After 96-hour incubation with each example compound in MIA-PACA2 cells, the cell proliferation of each sample was measured using the MTS Cell Titre 96 Aqueous One Solution Cell Proliferation Assay (Promega Ltd). The percentage of inhibition was calculated against the mean of the DMSO treated controls samples.

TABLE 1

Cell growth inhibition data for pancreatic cancer cell line panel for Examples 1 to 8; $IC_{50}$ (nM) values from 96 hr MTS assays. The data shows that Examples 1 to 8 show varying ability to inhibit cancer cell growth. In particular example compound 1 is the most active in the group.

| Example compound | Rel $IC_{50}$ | ABS $IC_{50}$ |
| --- | --- | --- |
| 1 | 0.035 | 0.056 |
| 2 | 0.188 | 0.292 |
| 3 | 0.282 | 0.284 |
| 4 | 0.132 | 0.175 |
| 5 | 0.239 | 0.180 |
| 6 | 0.099 | 0.102 |
| 7 | 0.117 | 0.182 |
| 8 | 0.174 | 0.277 |

In Vivo Xenograft Efficacy Studies

Mice aged 5-7 weeks weighing approximately 25-32 g were implanted for the study and purchased from Charles River. The pancreatic tumour cell implantation procedure involved MIA-PACA2 cells (1×10$^7$ in Matrigel) being implanted subcutaneously using a 22-gauge needle onto the rear flank of the mice. Parameters evaluated include: tumour size and animal bodyweight. Tumour volume was measured three times weekly and bodyweight at least 3 times weekly. Allocation to treatment groups was done randomly when tumours reached approximately 50 mm$^3$ for animals in the efficacy study. Animals (female athymic nude mice bearing MIA-PACA2 tumours) were IV dosed for 28 days, twice weekly, at doses of 10 and 15 mg/kg for C1, and at doses of 0.5 and 1.0 mg/kg for Example 1, on account of its 10-fold greater cellular potency. Each group comprised 8 animals. All protocols used in this study were approved by the appropriate Animal Welfare and Ethical Review Board, and all procedures were carried out under the guidelines of the UK Animal (Scientific Procedures) Act 1986. Results are shown in the tables below and FIG. 1.

Example 1

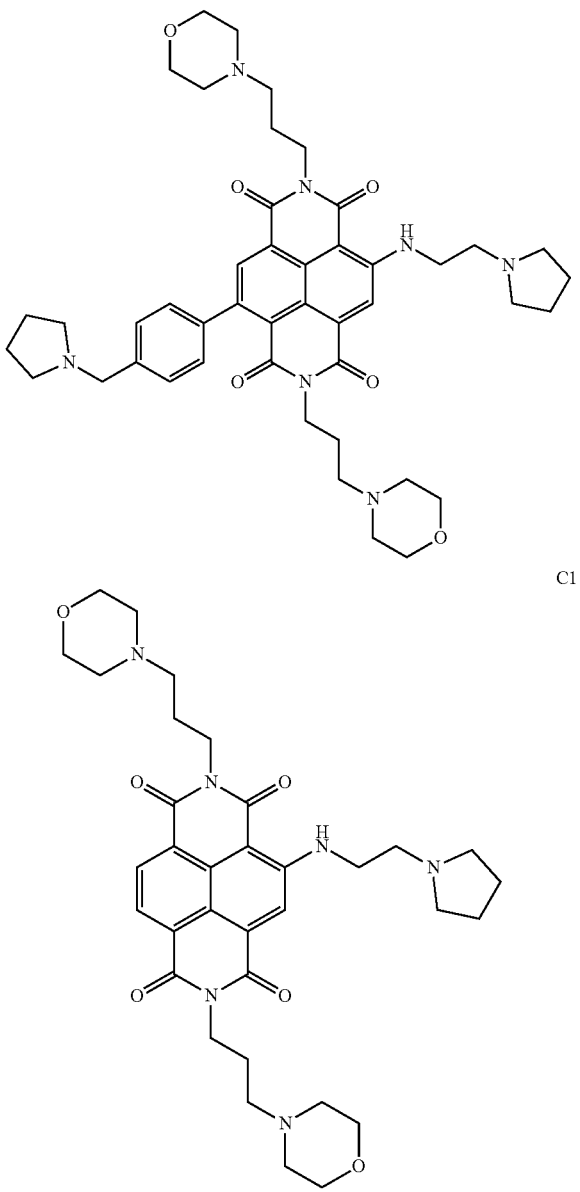

C1

TABLE 2

Basic properties and in vitro GQ binding data of Example 1 compared with prior art compound C1 (with reference to WO2017/103587A1)

| | Example 1 | C1 |
|---|---|---|
| Mol wt | 791.99 | 632.33 |
| clogP | 5.65 | 3.72 |
| Fluorescence excitation and emission max, in nm | 510, 612 (em) 510 (ex) | 510, 590 (em) 510 (ex) |
| Formulation of free base, for cellular and in vivo studies, up to MTD | Acidified phosphate-buffered saline (PBS) | Acidified phosphate-buffered saline (PBS) |
| Salt and aqueous solubility | Not made | HCl/formate salt: >5 mg/ml |
| Stability in saline at 0° C. | >1 month | >1 month |
| $t_{1/2}$ mouse microsomal stability, min | 268 | >480 |

TABLE 2-continued

Basic properties and in vitro GQ binding data of Example 1 compared with prior art compound C1 (with reference to WO2017/103587A1)

| | Example 1 | C1 |
|---|---|---|
| Plasma protein binding % in vitro | 66.1 | 35 |
| In vitro blood/plasma partitioning | 6.1 | 10.9 |
| FRET $\Delta T_m$, ° C. with GQ | 23.1 | 17.6 |

TABLE 3

Cell growth inhibition data for pancreatic cancer cell line panel for Example 1 compared with prior art compound C1 (with reference to WO2017/103587A1); $IC_{50}$ (nM) values from 96 hr SRB assays, as detailed in our previous publications and disclosures. The data shows that Example 1 is a significantly more potent compound in terms of its ability to inhibit cancer cell growth, and that its pharmacological properties are at least comparable.

| | Example 1 | C1 |
|---|---|---|
| MIA-PACA2 | 1.3 | 13.0 |
| PANC-1 | 1.4 | 15.6 |
| CAPAN-1 | 5.9 | 26.5 |
| BX-PC3 | 2.6 | 15.5 |
| MIA-PACA2$^{gemR}$ | 3.8 | 14.9 |

The graph in FIG. 1 shows the Xenograft data in the MIA-PACA2 model, after 28 days IV administration, followed by 28 days measurement (performed by AXIS BioServices). The data shown is mean±SD n=8 up to day 23 and n=4 to the end of the study. The data shows that the compound of Example 1 inhibited the growth of the pancreatic tumour and reduced the tumour's size considerably more than the comparative compound C1 or the known anti-cancer drug, Gemcitabine, did, even at a once-weekly dosing regimen. Furthermore, Example 1 and the dosing schedules were well-tolerated showing no sign of adverse effects. The starting tumour volumes were 0.4 mm³. Example 1 was active in both of the dosage regimens examined, 1× weekly and 2× weekly, both at a 1 mg/kg dose. Both had 5/8 complete regression in tumour volume at the end of the dosing period. In the complete regression cohorts, tumours have completely disappeared and no regrowth seen after 28 days post-dosing. A minority of tumours in the C1 and Example 1 groups do not show complete regression, but do show reductions in tumour growth, leading to consistently smaller volumes than in the vehicle control groups.

XTT Assay

The CyQUANT XTT Cell Viability Assay (Invitrogen) is a complete, optimized assay that generates a consistent colorimetric detection of viable mammalian cells. The assay kit consists of two reagents, XTT Reagent (2,3-bis-(2-methoxy-4-nitro-5-sulfophenyl)-2H-tetrazolium-5-carboxanilide) and Electron Coupling Reagent. XTT Reagent is used to assess cell viability as a function of cellular redox potential, and the electron coupling reagent improves the dynamic range of the assay. The kit was used as per the manufacturers' instructions.

TABLE 4

Cell growth inhibition data for prostate cancer cell line panel for Example 1 compared with prior art compound C1 (with reference to WO2017/103587A1), and clinically-approved hormonal prostate cancer therapeutic agents Abiraterone and Enzalutamide; IC50 (nM) values from 72 hr XTT assays. The data shows that the compound of example 1, is highly active in a panel of prostate cancer cell lines, notably in the metastatic and androgen-independent PC-3 line, when compared to the C1 and even more so when compared to the two clinically used drugs.

|       | Example 1 | C1  | Abiraterone | Enzalutamide |
|-------|-----------|-----|-------------|--------------|
| PC-3  | 3         | 94  | 4820        | 5350         |
| DU145 | 32        | 113 | N/A         | N/A          |
| LNCaP | 247       | 394 | 3860        | 4820         |
| VCaP  | 68        | 135 | N/A         | N/A          |
| 22RV1 | 90        | 90  | N/A         | N/A          |

In summary, the compounds of the invention show anti-tumour activity in a number of cancer cell lines.

The invention claimed is:

1. A compound of Formula I:

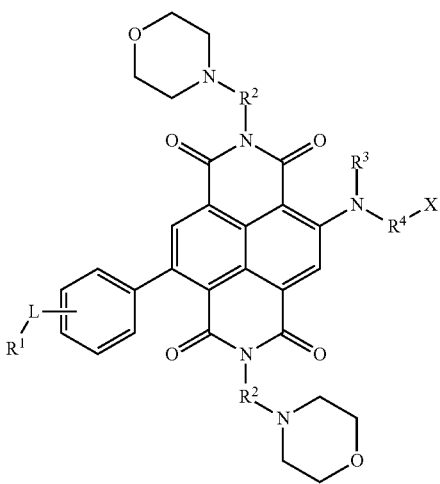

Formula I

L is in the meta or para position of the phenyl ring and is selected from the group consisting of $(CH_2)_{1-6}$ and $(CH_2)_{1-5}NH$;

$R^1$ is selected from the group consisting of optionally substituted $C_{5-7}$cycloalkyl, optionally substituted nitrogen-containing 5-7 membered heterocycloalkyl and $NR^9R^{10}$;

$R^2$ and $R^4$ are independently selected from the group consisting of straight and branched chain $C_{1-6}$-alkanediyl;

$R^3$, $R^9$ and $R^{10}$ are independently selected from the group consisting of H or $C_{1-6}$ alkyl;

X is selected from the group consisting of halo, $OR^5$, $NR^6_2$, $CONR^7_2$, $COOR^8$, H and $COR^8$;

$R^5$ is selected from the group consisting of H, $C_{1-6}$ alkyl, $C_{4-7}$ cycloalkyl, 4-7 membered heterocycloalkyl and aryl;

$R^6$ is selected from the group consisting of H, $C_{1-6}$ alkyl, aryl and, $C_{1-12}$-aralkyl, or the groups $R^6$ together with the N-atom to which they are attached form a N-containing, saturated 4-7 membered heterocyclic group;

the groups $R^7$ are each selected from H and $C_{1-6}$ alkyl groups or the groups $R^7$ together with the N atom to which they are attached form a 4-7 membered heterocyclic group;

$R^8$ is selected from the group consisting of $C_{1-6}$ alkyl, $C_{7-12}$ aralkyl, and aryl; and salts, hydrates and solvates thereof.

2. The compound according to claim 1, wherein L is $(CH_2)_{1-6}$.

3. The compound according to claim 1, wherein $R^1$ is a nitrogen-containing 5-7 membered heterocycloalkyl optionally selected from the group consisting of pyrrolidinyl, imidazolidinyl, pyrazolidinyl, piperidinyl, piperazinyl, morpholinyl, azepanyl, and diazepanyl.

4. The compound according to claim 1, wherein L is $(CH_2)_{1-5}NH$ and $R^1$ is a $C_{5-7}$cycloalkyl.

5. The compound according to claim 1, wherein L is in the para position.

6. The compound according claim 1, wherein $R^2$ is a straight chain $C_{2-4}$ alkanediyl.

7. The compound according to claim 1, wherein $R^3$ is H.

8. The compound according to claim 1, wherein $R^4$ is a straight or branched chain $C_{2-4}$ alkanediyl.

9. The compound according to claim 8, wherein $R^4$ is a straight chain $C_{2-4}$ alkanediyl.

10. The compound of claim 1, wherein X is $NR^6_2$.

11. The compound of claim 10, wherein the $R^6$ groups together with the nitrogen atom to which they are attached form a heterocyclic group selected from the group consisting of 4-methyl piperazine-1-yl, morpholine-4-yl, pyrrolidin-1-yl, pyridin-2-yl and piperidin 1 yl.

12. The compound of claim 1, wherein the compound is selected from the group consisting of:

2,7-bis(3-morpholinopropyl)-4-((2-(pyrrolidin-1-yl)ethyl)amino)-9-(4-(pyrrolidin-1-ylmethyl)phenyl)benzo[lmn][3,8]phenanthroline-1,3,6,8(2H,7H)-tetraone;

4-(4-(morpholinomethyl)phenyl)-2,7-bis(3-morpholinopropyl)-9-((2-(pyrrolidin-1-yl)ethyl)amino)benzo[lmn][3,8]phenanthroline-1,3,6,8(2H,7H)-tetraone;

2,7-bis(3-morpholinopropyl)-4-((2-(pyrrolidin-1-yl)ethyl)amino)-9-(3-(pyrrolidin-1-ylmethyl)phenyl)benzo[lmn][3,8]phenanthroline-1,3,6,8(2H,7H)-tetraone;

2,7-bis(3-morpholinopropyl)-4-(4-(piperidin-1-ylmethyl)phenyl)-9-((2-(pyrrolidin-1-yl)ethyl)amino)benzo[lmn][3,8]phenanthroline-1,3,6,8(2H,7H)-tetraone;

4-(4-((diethylamino)methyl)phenyl)-2,7-bis(3-morpholinopropyl)-9-((2-(pyrrolidin-1-yl)ethyl)amino)benzo[lmn][3,8]phenanthroline-1,3,6,8(2H,7H)-tetraone;

4-(4-((cyclopentylamino)methyl)phenyl)-2,7-bis(3-morpholinopropyl)-9-((2-(pyrrolidin-1-yl)ethyl)amino)benzo[lmn][3,8]phenanthroline-1,3,6,8(2H,7H)-tetraone;

4-(4-(azepan-1-ylmethyl)phenyl)-2,7-bis(3-morpholinopropyl)-9-((2-(pyrrolidin-1-yl)ethyl)amino)benzo[lmn][3,8]phenanthroline-1,3,6,8(2H,7H)-tetraone;

4-bromo-2,7-bis(3-morpholinopropyl)-9-((2-(pyrrolidin-1-yl)ethyl)amino)benzo[lmn][3,8]phenanthroline-1,3,6,8(2H,7H)-tetraone; and salts, hydrates and solvates thereof.

13. The compound according to claim 1, wherein Formula I has the following structure of Formula II:

Formula II

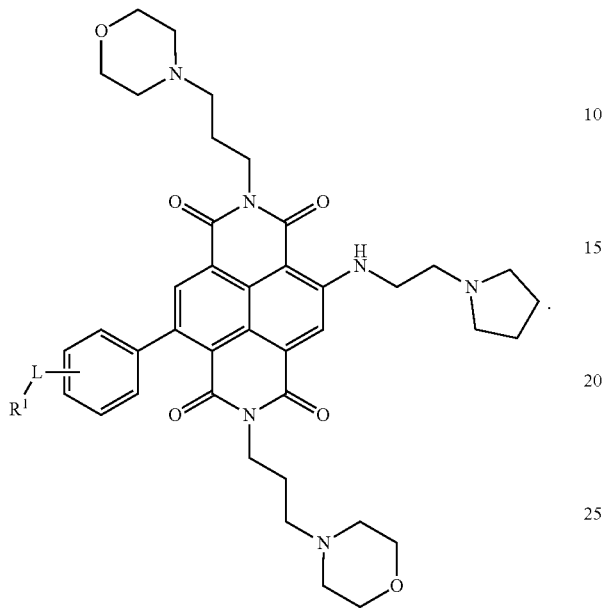

14. A pharmaceutical composition comprising the compound according to claim 1 or a salt, hydrate or solvate thereof, in combination with a pharmaceutically acceptable diluent or carrier.

15. A method of synthesising a substituted naphthalene diimide compound according to claim 1, comprising the steps of:

i) reacting a compound of Formula III in a nucleophilic substitution reaction with a compound of Formula IV:

Formula III

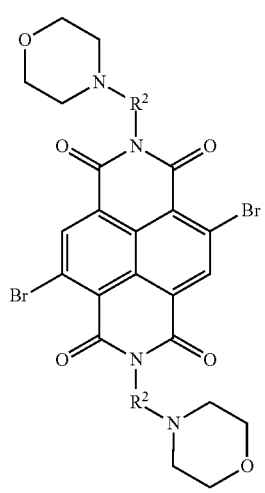

-continued

Formula IV

HN(R³)(R⁴X)

wherein at least one Br in the compound of Formula III is substituted by the nucleophilic amine nitrogen in the compound of Formula IV;

ii) reacting a compound of Formula V, obtainable from the product resulting from the nucleophilic substitution reaction of Formula III and Formula IV, with a compound of Formula VI:

Formula V

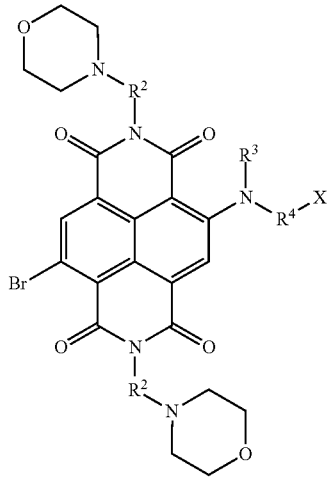

Formula VI

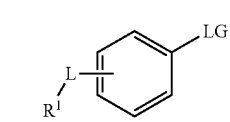

wherein an aryl-aryl bond is formed between the phenyl of Formula VI and the phenyl with the Br attached in the compound of Formula V, wherein the LG and Br are leaving groups, to make the compound of Formula I.

16. The compound according to claim 2, wherein L is $(CH_2)_{1-2}$.

17. The compound according to claim 3, wherein $R^1$ is pyrrolidinyl.

18. The compound according to claim 11, wherein the heterocyclic group is pyrrolidin-1-yl.

* * * * *

UNITED STATES PATENT AND TRADEMARK OFFICE
CERTIFICATE OF CORRECTION

PATENT NO. : 11,560,380 B2
APPLICATION NO. : 17/611890
DATED : January 24, 2023
INVENTOR(S) : Stephen Neidle et al.

It is certified that error appears in the above-identified patent and that said Letters Patent is hereby corrected as shown below:

On the Title Page

Page 3, Column 2, Line 17, delete "[Imn]" and insert --[lmn]--

Page 3, Column 2, Line 24, delete "[Imn]" and insert --[lmn]--

In the Claims

Column 24, Line 35, delete "piperidin 1 yl." and insert --piperidin-1-yl.--

Signed and Sealed this
Twenty-third Day of May, 2023

Katherine Kelly Vidal
*Director of the United States Patent and Trademark Office*